(12) United States Patent
Christensen

(10) Patent No.: US 11,591,763 B2
(45) Date of Patent: Feb. 28, 2023

(54) SYSTEMS AND METHODS FOR COASTAL DRAINAGE CONTROL

(71) Applicant: EcoShore Int'l, Inc., Boca Raton, FL (US)

(72) Inventor: Kenneth William Christensen, Boca Raton, FL (US)

(73) Assignee: EcoShore Int'l, Inc., Boca Raton, FL (US)

( * ) Notice: Subject to any disclaimer, the term of this patent is extended or adjusted under 35 U.S.C. 154(b) by 0 days.

(21) Appl. No.: 17/420,412

(22) PCT Filed: Jan. 2, 2020

(86) PCT No.: PCT/US2020/012071
§ 371 (c)(1),
(2) Date: Jul. 2, 2021

(87) PCT Pub. No.: WO2020/142619
PCT Pub. Date: Jul. 9, 2020

(65) Prior Publication Data
US 2022/0090340 A1    Mar. 24, 2022

Related U.S. Application Data

(60) Provisional application No. 62/787,788, filed on Jan. 3, 2019.

(51) Int. Cl.
*E02B 3/04*       (2006.01)
*F16K 15/03*      (2006.01)
(Continued)

(52) U.S. Cl.
CPC ............ *E02B 3/041* (2015.09); *F16K 15/034* (2021.08); *F16K 24/046* (2013.01); *F16K 31/18* (2013.01)

(58) Field of Classification Search
CPC .... E02B 3/04; E03F 5/042; E03F 2005/0417; F16K 21/18; F16K 24/042; F16K 24/044; F16K 24/046; F16K 31/22
See application file for complete search history.

(56) References Cited

U.S. PATENT DOCUMENTS 1,305,868 A    6/1919   Baun
3,227,173 A    1/1966   Bernstein
(Continued)

OTHER PUBLICATIONS

International Search Report and Written Opinion in International Application No. PCT/US2020/012071, dated Jun. 5, 2020 (10 pages).

*Primary Examiner* — Hailey K. Do
(74) *Attorney, Agent, or Firm* — Bookoff McAndrews, PLLC

(57) ABSTRACT

A drainage device includes a conduit extending from a bottom end toward a top end and a valve coupled to the conduit. The valve includes a first stop having an opening and an obstruction within the conduit. The obstruction, in a first configuration, may be spaced apart from the opening, enabling fluid to flow through the first stop and through the conduit. The obstruction, in a second configuration, may block the opening to prevent fluid flow through the first stop and through the conduit. The obstruction may move from the first configuration to the second configuration in response to (1) fluid pressure acting in a direction from the bottom end toward the top end of the conduit, or (2) when a fluid having a higher density than the obstruction is disposed within the valve.

15 Claims, 10 Drawing Sheets

(51) Int. Cl.
*F16K 24/04* (2006.01)
*F16K 31/18* (2006.01)

(56) References Cited

U.S. PATENT DOCUMENTS

| | | |
|---|---|---|
| 3,675,248 A | 7/1972 | Gaj |
| 3,973,407 A * | 8/1976 | Vecchio ............... E03F 5/042 |
| | | 210/136 |
| 4,314,583 A | 2/1982 | Peterson |
| 5,087,483 A | 2/1992 | Vargo |
| 5,429,149 A | 7/1995 | Mittell et al. |
| 5,662,138 A | 9/1997 | Wang |
| 5,797,426 A | 8/1998 | Powell |
| 6,626,201 B1 | 9/2003 | Kim |
| 7,325,839 B2 | 2/2008 | Slentz |
| 10,072,409 B2 | 9/2018 | Nishiyama |
| 2003/0077122 A1 * | 4/2003 | Carnahan ............. E02B 3/04 |
| | | 405/21 |
| 2007/0068390 A1 | 3/2007 | Cho |
| 2007/0215212 A1 * | 9/2007 | Demeniuk ........... E03F 5/042 |
| | | 137/362 |
| 2012/0004623 A1 | 1/2012 | Tumminaro et al. |
| 2012/0192950 A1 | 8/2012 | Huber |
| 2012/0237760 A1 * | 9/2012 | Imsgard ............... C08L 53/00 |
| | | 524/505 |
| 2013/0022399 A1 * | 1/2013 | Pierce, Jr. ............. E02B 3/04 |
| | | 405/31 |
| 2015/0056016 A1 * | 2/2015 | Popa .................... E02B 1/00 |
| | | 405/30 |

\* cited by examiner

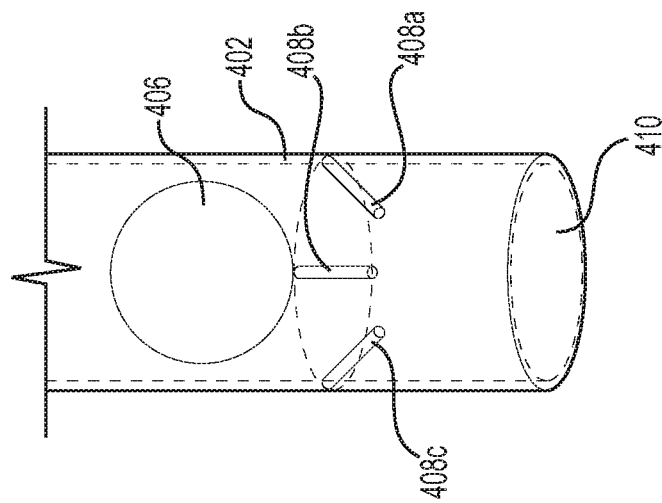
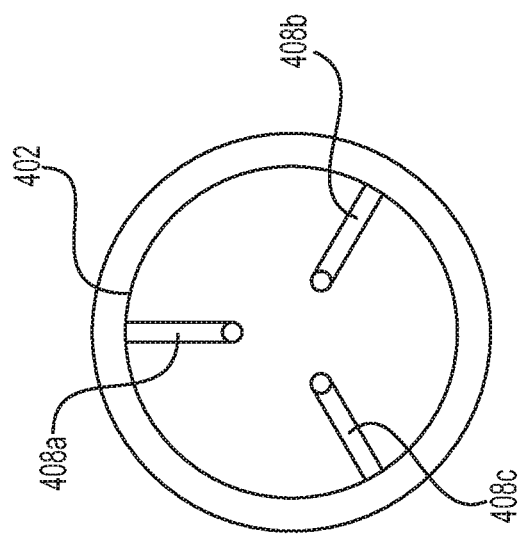

SYSTEMS AND METHODS FOR COASTAL DRAINAGE CONTROL

CROSS-REFERENCE TO RELATED APPLICATION(S)

This patent application claims the benefit under 35 U.S.C. § 119 to U.S. Provisional Application No. 62/787,788, filed on Jan. 3, 2019, the entirety of which is incorporated herein by reference.

TECHNICAL FIELD

Various embodiments of the present disclosure relate generally to the field of water drainage and, more particularly, to systems and methods for controlling water drainage in coastal areas by equalizing pressure.

BACKGROUND

Passive drainage systems exist to assist with beach drainage in coastal areas, resulting in reduced beach erosion or sand accretion. Although the existing devices are effective overall, there are several drawbacks that, if eliminated, would enhance the efficacy of such devices.

SUMMARY OF THE DISCLOSURE

In one aspect, a drainage device is disclosed. The drainage device may include: a conduit extending from a bottom end toward a top end; and a valve coupled to the conduit. The valve may include: a first stop, the first stop having an opening; and an obstruction within the conduit, wherein: in a first configuration, the obstruction may be spaced apart from the opening, enabling fluid (e.g., air or water) to flow through the first stop and through the conduit; and in a second configuration, the obstruction may be configured to block the opening to prevent fluid flow through the first stop and through the conduit, wherein the obstruction is configured to move from the first configuration to the second configuration in response to (1) fluid pressure acting in a direction from the bottom end toward the top end of the conduit, or (2) when a fluid having a higher density than the obstruction is disposed within the valve.

Any of the drainage devices described herein may have any of the following features. The obstruction is a ball having a diameter larger than a diameter of the opening of the first stop in the top of the valve. The valve may include: a second stop in the bottom of the valve, wherein the obstruction is positioned between the first stop and the second stop, and the second stop is configured to maintain the obstruction in the valve, and also is configured to allow fluid to flow through the second stop. The second stop is a rod, a beam, a pin, several pins, or a screen. The obstruction is configured to transition from the second configuration (being closed) to the first configuration (being open) when the fluid pressure acting in the direction from the bottom end toward the top end of the conduit is less than a force of gravity acting on the obstruction. The drainage device does not include any electronic component. The drainage device is configured to operate the obstruction to open and close the opening of the first stop based on an electrical signal; and/or wherein the obstruction is configured to automatically open or close the first stop based on a predetermined weather condition or an unusual weather condition requiring one way pressure equalization. The drainage device may include a flexible tube in fluid communication with the conduit, and extending away from the top end of the conduit. The drainage device may include a filter coupled to the flexible tube, wherein the filter is fluid-permeable and is configured to prevent debris from entering the flexible tube. The flexible tube may include a perforation between a first part and a second part of the flexible tube, wherein the first part of the tube is directly coupled to the conduit, wherein, in response to a pulling force applied to the second part of the flexible tube, the second part is configured to separate from the first part at the perforation. The drainage device may include a first filter coupled to the first part of the flexible tube, and a second filter coupled to the second part of the flexible tube, wherein each of the first filter and the second filter is fluid-permeable and is configured to prevent debris from entering the first part and the second part, respectively. The conduit is hollow and includes a plurality of openings extending through an outer surface and an inner surface of the conduit, wherein fluid is configured to fill up the tube and flow through the openings. The drainage device may include a pointed tip extending away from the bottom end of the conduit. The drainage device may include two or more flaps at or adjacent the bottom end of the conduit, wherein: each flap includes a first end and a second end, wherein the second end of each flap is positioned closer to the top end of the conduit than the first end of each flap; and the second end of each flap is positioned further away from an outer surface of the conduit than the first end of each flap. The drainage device may include one or more blocking members, wherein: each of the one or more blocking members is disposed between the outer surface of the conduit and one of the two or more flaps; and each of the one or more blocking members is configured to prevent the one of the two or more flaps from extending substantially parallel to the outer surface of the conduit. The drainage device may be made substantially from natural materials, the natural materials being wood or bamboo. The drainage device may comprise materials that are impregnated using $CO_2$.

In another aspect, a drainage device is disclosed. The drainage device may include: a conduit extending from a bottom end toward a top end; and a valve coupled to the conduit. The valve may be configured to: in a first configuration, enable fluid to flow through the valve and through the conduit from the top end toward the bottom end (downwards flow); and in a second configuration, prevent fluid flow through the valve and through the conduit (upwards flow). The drainage device may further include a flexible tube in fluid communication with the conduit, and extending away from the top end of the conduit. The flexible tube may include a perforation between a first part and a second part of the flexible tube. The first part of the tube may be directly coupled to the conduit; and in response to a pulling force applied to the second part of the flexible tube, the second part is configured to separate from the first part at the perforation.

Any of the drainage devices described herein may have any of the following features. The drainage device may include a first filter coupled to the first part of the flexible tube, and a second filter coupled to the second part of the flexible tube, wherein each of the first filter and the second filter is fluid-permeable and is configured to prevent debris from entering the first part and the second part, respectively. The conduit is hollow and includes a plurality of openings extending through an outer surface and an inner surface of the conduit, wherein fluid is configured to fill up the hollow space and flow through the plurality of openings.

In yet another aspect, a method of controlling drainage of a coastal area is disclosed. The method may include; inserting a bottom end of a drainage device below a sea floor; and positioning a flexible tube at a top end of the drainage device above the sea floor at a first position, wherein during low tide and high tide, the flexible tube is arranged to be continuously submerged by seawater; wherein, during a transition from high tide to low tide, water from the coastal area is configured to flow through a beach and drainage devices, via the coarser layers, and out of the drainage device furthest out below the sea floor, and via the flexible tube into the open water above the sea floor.

Any of the drainage devices described herein may have any of the following features. The flexible tube is water soluble, and is configured to dissolve about one to three months after installation of the drainage device or it is camouflaged.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 4C is an end view of an alternative activatable valve for a drainage control module, according to one or more embodiments.

FIG. 4D is a schematic view of the valve of FIG. 4C.

DETAILED DESCRIPTION OF EMBODIMENTS

Figure 1:
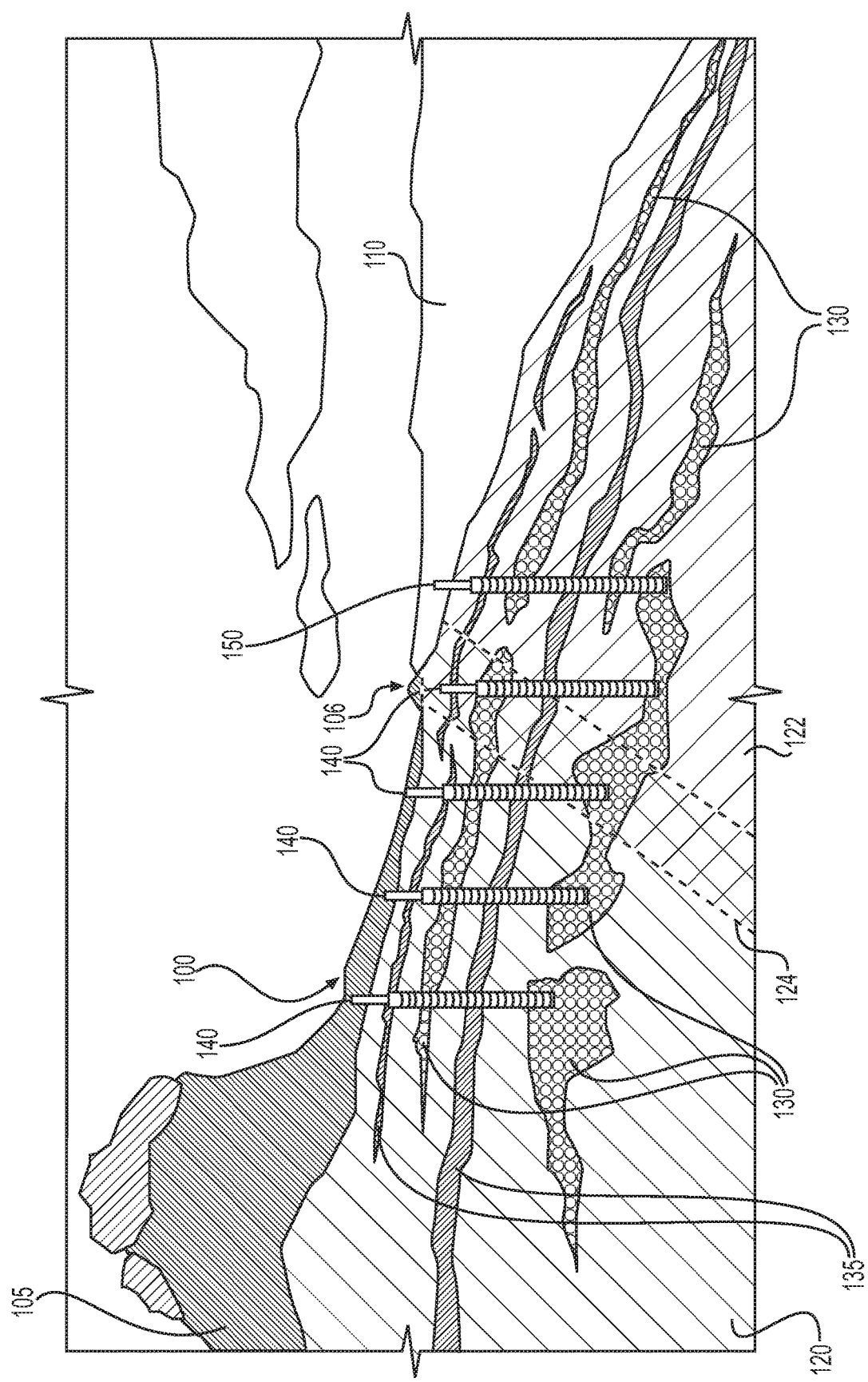
FIG. 1 depicts an exemplary coastal environment with a drainage control system, according to one or more embodiments.

While principles of the present disclosure are described herein with reference to illustrative embodiments for particular applications, it should be understood that the disclosure is not limited thereto. Those having ordinary skill in the art and access to the teachings provided herein, will recognize that the features illustrated or described with respect to one embodiment, may be combined with the features of another embodiment. Therefore, additional modifications, applications, embodiments, and substitution of equivalents, all fall within the scope of the embodiments described herein. Accordingly, the disclosure is not to be considered as limited by the foregoing description.

The terminology used below may be interpreted in its broadest reasonable manner, even though it is being used in conjunction with a detailed description of certain specific examples of the present disclosure. Indeed, certain terms may even be emphasized below; however, any terminology intended to be interpreted in any restricted manner will be overtly and specifically defined as such in this Detailed Description section. Both the foregoing general description and the following detailed description are exemplary and explanatory only and are not restrictive of the features, as claimed.

As used herein, the terms "has," "include," "having," "including," or other variations thereof, are intended to cover a non-exclusive inclusion such that a process, method, article, or apparatus that has a list of elements does not include only those elements, but may include other elements not expressly listed or inherent to such a process, method, article, or apparatus.

In this disclosure, relative terms, such as, for example, "about," "substantially," "generally," and "approximately" are used to indicate a possible variation of ±10%, ±20%, ±30% or more, in a stated value.

The term "exemplary" is used in the sense of "example" rather than "ideal." As used herein, the singular forms "a," "an," and "the" include plural reference unless the context dictates otherwise.

The following discussion relates to systems and methods for providing effective water drainage in coastal areas for controlling beach erosion. For example, a pressure equalization module (PEM) may include a rigid plastic tube. The rigid plastic tube may include a solid top part and a main bottom part with small slits that keep sand and debris out of the tube, but allow water to enter the tube. In a passive drainage system according to the present disclosure, the PEMs may be inserted in a beach in rows from the dune foot to the mean low waterline. That is, the bottom part with small slits extends down into the freshwater table, vertically connecting different strata underneath the top sand layer of the beach. During falling tides, water will automatically drain via the layer with the least resistance, typically a coarser layer, and an opening in the top of the PEM allows air in as water escapes, equalizing the pressure.

Such systems and methods may utilize an activatable valve to regulate the flow of air and water based on various tidal and coastal weather conditions.

The passive drainage system described above may allow water to drain effectively from a beach by equalizing pressure (e.g., vacuum) under the beach. However, during rising tides, storms, king tides, or various other coastal weather conditions, the waves may travel farther inland due to the fact the pressure under the beach has been equalized. Because there is no (or relatively little) pressure building up in the beach, the back beach may be flooded when the waves advance farther inland. Indeed, excess water on the back beach during a period of storm or other coastal weather conditions may result in suspended beach and/or loss of beach sand. Further, a beach with the passive drainage system may have larger fluctuations in sand elevation during changing weather conditions which may lead to exposed drainage modules. The exposed drainage modules may get filled with sand, for example, if the slits on the drainage module become exposed to moving water, which may render the exposed drainage modules ineffective. As such, the above-described negative effects of the passive drainage system may on several occasions outweigh the positive effects of the pressure equalization during falling tides.

However, if the negative effects are eliminated or reduced, the net effect of the passive drainage system may be multiplied.

To address these phenomena, the present disclosure contemplates a drainage control module that may utilize an activatable valve to restrict the flow of air or water in one direction during, for example, special tidal and coastal weather conditions, while allowing free flow of air or water in the opposite direction for creating a one-direction (unidirectional) pressure equalization. For example, the valve in the module may restrict air or water moving in an upward direction to the top of the module. If water moves rapidly inland due to a storm, large waves, or other coastal weather conditions, the beach may behave like a normal beach without any drainage system, thereby restricting excessive flow of water inland. However, during falling tides, the valve may open and allow air or water to travel freely down into the module to promote water drainage.

Various non-limiting embodiments of the present disclosure will now be described to provide an overall understanding of the principles of methods and systems contemplating a module with a valve to regulate the flow of air and water based on various coastal environmental conditions.

FIG. 1 depicts a drainage-controlled coastal environment that may include a coastal profile 100, a top sand layer 105 that is primarily dry, a freshwater outflow zone 120 (freshwater zone), a salt water tongue 122, a mixing zone 124, coarser layers 130, sedimentary layers 135, sea water 110, modules 140, and seaward modules 150. The top sand layer 105 may accumulate sand, as sand is fed to a beach face 106 by the waves and eventually to the coastal profile 100 by wind. The sedimentary layers 135 will be formed under the top sand layer 105 when the movement of the tide results in a sorting of the particles. The sedimentary layers 135 may be impermeable or semi-permeable and may reduce hydraulic conductivity of water between the sedimentary layers 135, especially if fine particles (e.g., clay) are present. For example, during rising tide, the sea water 110 may be pushed into the beach and extend the heavier salt water tongue 122 into the fresh water zone 120 at the mixing zone 124, elevating the groundwater level in the freshwater zone 120 toward the top sand layer 105 and further inland. During falling tide, the elevated groundwater may drain back down and out to sea due to gravity. However, the water may drain slowly if sedimentary layers 135 are impermeable or semi-permeable, restricting access to coarser layers where water can drain freely, and to air, that shall replace escaping water. The slow water drainage may leave the beach face 106 wet longer and result in reduced sand deposits, and increase erosion. However, other layers, such as the coarser layers 130, which may be primarily coarse in the form of gravel and pebbles, may allow water to drain faster. The modules 140 may be installed by penetrating through the top sand layer 105 and into different layers underneath the top sand layer 105, vertically connecting the different layers including the coarser layers 130. As such, the modules 140 may allow water to drain faster via the coarser layers 130 as air enters an opening at the top of the module 140 to equalize pressure.

Figure 2:
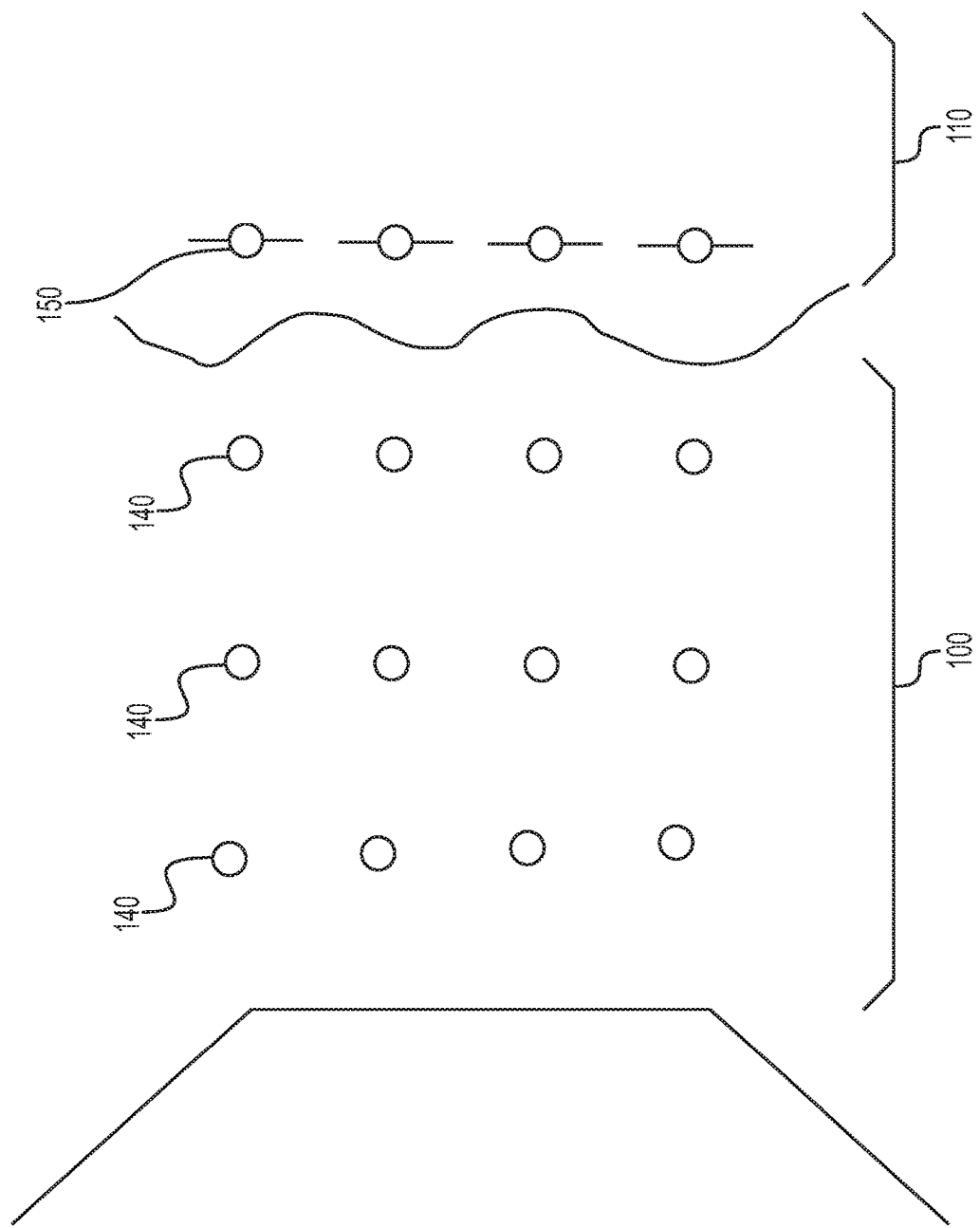
FIG. 2 depicts a top-down view of an exemplary drainage-controlled coastal environment, according to one or more embodiments.

FIG. 2 shows a top-down view of the drainage-controlled coastal environment, according to an exemplary embodiment of the present disclosure, with the modules 140 installed under the coastal profile 100 of a beach. The modules 140 may be placed about 30 cm to about 90 cm (about 1 foot to about 3 feet) below the surface of the top sand layer 105. However, it is contemplated that lower or higher values may be utilized. For example, the modules may be placed about 90 cm below the surface to be out of reach for turtles, and may be placed even lower if the top layer of dry sand is thick. Further, the modules 140 may be installed in rows from the dune to the lower low waterline. The seaward modules 150 may be installed closest to the sea, and the top of the seaward modules 150 may protrude from the bottom of the seafloor and into the open sea water 100, ensuring that the seaward modules 150 are always under water. The seaward modules 150 may or may not include an activatable valve. The seaward modules 150 may include some or all of the features of the modules 140.

The number of rows of the modules 140 installed and the distance between each of the modules 140 in the drainage system, according to the present disclosure, may vary based on the geographical and other environmental conditions of the beach and the coastal profile 100. Depending on the specific conditions on a given beach, only the module 140 closest to the dune may have the one-direction equalization function, or several modules 140 on a dry beach may have the one-direction equalization function.

Figure 3:
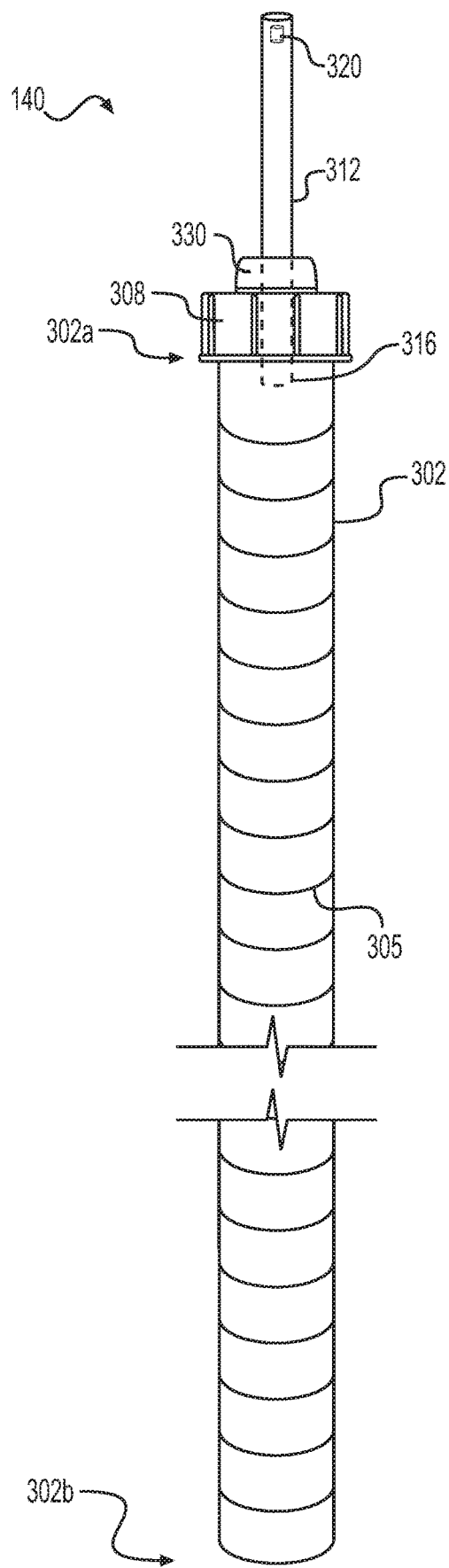
FIG. 3 depicts an exemplary hollow drainage control module, according to one or more embodiments.

FIG. 3 depicts an exemplary module 140, according to the present disclosure. The module 140 may include a hollow tube 302 configured to allow air and water to flow through the tube 302. Further, the tube 302 may be open at a proximal end 302*a* and at least partially closed at a distal end 302*b*. The tube 302 may include hard plastic or metal, or any other suitable material, such as, e.g., wood. The tube 302 may have a plurality of slits 305 (or a perforation) configured to allow water to flow through the tube 302, but substantially prevent sand or debris from entering the tube 302. As shown in FIG. 3, slits 305 may extend only partially around a circumference of body 302 (i.e., circumferentially or in a circumferential direction about body 302). As shown, slits 305 may be spaced apart from one another about a longitudinal axis 302*c* of body 302. In other embodiments, multiple slits 305 may be spaced apart from one another along a same circumference of body 302. In other embodiments, slits 305 may extend vertically along longitudinal axis 302*c* and may be spaced apart from one another in the circumferential direction.

The module 140 may further include a cap 308 coupled to the opening of the tube 302 at the proximal end 302*a*. The module 140 may further include a housing 330. A valve 310 (shown in FIGS. 4A-B) may be arranged within the housing 330. The housing 330 may be coupled to or integrated with the cap 308, or may be arranged within other portions of the module 140. The module 140 may further include a first flexible tube 312 and a second flexible tube 316. The first flexible tube 312 and the second flexible tube 316 may be coupled to the housing 330 and/or the valve 310 that may be arranged within the housing 330. The housing 330 connecting the first flexible tube 312 and the second flexible tube 316 may be a hose connector configured to be arranged between two separate hoses to allow fluid communication between the two separate hoses. The valve 310 also may be coupled to or arranged within the housing 330, the first flexible tube 312, and/or the second flexible tube 316. In another embodiment, a single flexible tube may be provided instead of the first flexible tube 312 and the second flexible tube 316. The single flexible tube may be directly coupled to the cap 308, and one or several valves 310 may be arranged within the single flexible tube. Each valve within the single flexible tube may be tailored to close when a specific condition is fulfilled. For example, a valve that may be arranged closest to the bottom of the single flexible tube may close at or during high velocity flow, and a valve arranged in the middle portion of the single flexible tube may close if the valve is submerged in salt water (when a density of a ball inside valve 310 (explained in further detail below) is 1.01 or similar). Further, a valve that may be arranged in the top portion of the single flexible tube may close if the valve is submerged in saltwater or freshwater and the density of the valve is less than 1. The exemplary valve operations will be discussed in greater detail below.

In some embodiments, module 140 does not include any electronic device. In other embodiments, however, it is contemplated that module 140 does include one or more electronic components.

The first flexible tube 312 may have an upper opening and a lower opening. The first flexible tube 312 may receive or otherwise include a filter 320 inside of the first flexible tube 312. Filter 320 may be any suitable filter, including, e.g., plastic, steel wool, screens, or the like. The filter 320 may be arranged adjacent to the upper opening of the first flexible tube 312. The filter 320 may prevent sand and debris from entering the first flexible tube 312, while allowing gas and liquid (e.g., air and water) to pass through. The filter 320 may be made of materials including, for example, non-woven material that is resistant to scaling, for example, polyethylene (PE), high-density polyethylene (HDPE), polypropylene (PP), nylon, or any other suitable material that is resistant to scaling. The filter 320 may be removable for cleaning. For example, if the filter 320 gets blocked due to scaling or other debris, the filter 320 may removed from the first flexible tube 312 and cleaned. Pressure can be applied to the filter 320 by squeezing to remove any scaling or debris. The filter 320 may then be inserted back into the first flexible tube 312. In another embodiment, the module 140 does not include the valve 310 and the first flexible tube 312 may be coupled directly to the cap 308.

Figure 4B:
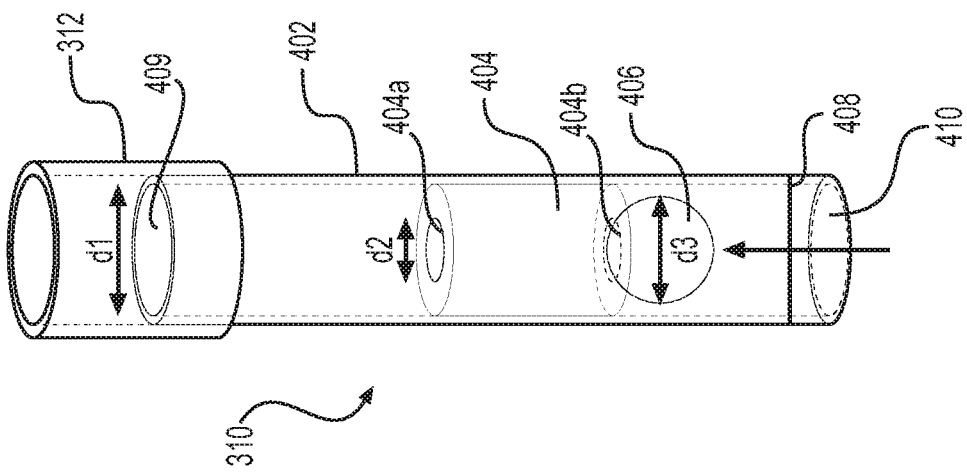
FIGS. 4A-4B depict exemplary schematics of an activatable valve for a drainage control module, according to one or more embodiments.
Figure 4A:
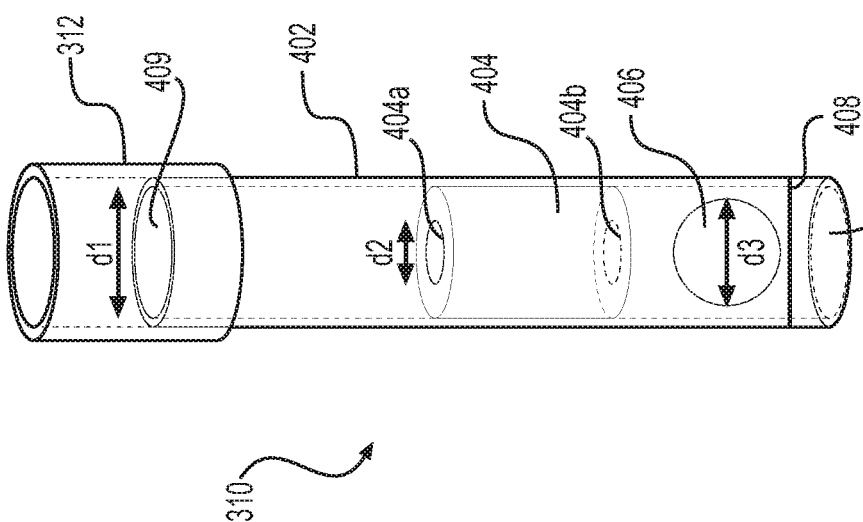

FIGS. 4A-4B depict a schematic of the valve 310, according to the present disclosure. The valve 310 may have a tube or conduit 402 coupled to the first flexible tube 312. The conduit 402 may have an upper opening 409 and a lower opening 410. Further, the valve 310 may include a first stop 404, a ball 406, and a second stop 408. The first stop 404 may be ring-shaped or tube-shaped. The ball 406 may be arranged longitudinally between the first stop 404 and the second stop 408. The second stop 408 may be a rod, a pin, one or more pins (e.g., three pins), a beam, a screen, or any other suitable structure that enables fluid flow therethrough, while also preventing the ball 406 from passing through the lower opening 410 of the conduit 402.

The first stop 404 may be a conduit disposed within conduit 402, and the first stop 404 may have an upper hole or opening 404a and a lower hole or opening 404b each with a diameter d2 (which may be, e.g., about 6 to about 7 mm, although any other suitable dimension is contemplated) that is smaller than the diameter d3 (which may be, e.g., about 6.5 mm to about 8.5 mm) of the ball 406. It is also contemplated that the first stop 404 may be otherwise integrated into the body of the conduit 402 and may include only or exactly one opening (instead of two openings as shown). For example, the stop 404 may be in the form of a ring, or any other form, that may include exactly one opening having the diameter d2. The diameter d2 of the stop 404 is smaller than the diameter d3 of the ball or movable obstruction 406 so that, when acted upon by water pressure in the upward direction (i.e., in a direction from the lower opening 410 toward the upper opening 409), the ball 406 plugs the hole 404b, preventing the flow of any fluid or air through the valve 310. In other words, the ball 406 may close the lower opening 404b of the first stop 404 and prevent air or water from flowing through the module 140 during, e.g., rising tide, king tide, or storm conditions. Further, the conduit 402 may have a diameter d1 (e.g., about 9 to about 12 mm) greater than the diameter d3 of the ball 406 so as to allow the ball 406 to travel freely within the tube 402 between the first stop 404 and the second stop 408.

The first stop 404 may operate between, for example, about −20 to about 90 degrees Celsius, and may include a chemically resistant material. Of course, this temperature range is only exemplary, and it is contemplated that first stop 404 may operate in other temperatures as well. The first stop 404 may also include a material that is non-stick to lime/scaling, sand, mud, and other organic materials. Further, the first stop 404 may be coupled to the conduit 402 using glue or any other adhesive that is tolerant to coastal elements and weather conditions. Alternatively, first stop 404 may be inserted into the conduit 402 by a friction fit, a screw, or a pin, or may be integral with the conduit 402. The first stop 404 may include a material that is non-stick to the ball 406. Furthermore, the ball 406 may operate in the same temperature range as the first stop 404, and also may include a chemically resistant material and preferably be hydrophilic. The ball 406 may include a material that is non-stick to lime/scaling, sand, mud, and other organic materials. The ball 406 may also be abrasion resistant and may include a material that is non-stick to the first stop 404. The density of the ball 406 may be variable to operate the valve 310 differently based on the desired mode of operation.

Saltwater is denser than freshwater because it contains salt (e.g., 21-30 kg per 1000 liter). As such, saltwater may have varying density (e.g., 1.021-1,030) depending on the location. In one example, when the density of the ball 406 is greater than the density of saltwater, e.g., 1.04 or more, the force from the flow of fluid entering the valve 310 (in the direction from bottom to top) will force the ball upwards and close the valve 310. However, as soon as the force is reduced, the ball 406 will fall down on the second stop 408 and the valve 310 will open. In another example, when the ball 406 has a lower density (e.g., 1.010) than the saltwater, the ball may rise and close the valve 310 when the ball 406 is simply surrounded by saltwater during rising tide. During falling tide, however, the ball 406 may become surrounded by freshwater with a lower density than the ball. Since the ball 406 having density greater than 1 is heavier than the freshwater, the ball 406 will fall down onto the second stop 408 and open the valve 310 independent of velocity. In yet another example, if the density of the ball 406 is less than 1, the ball 406 will float and always close the valve 310 if it is surrounded by water, regardless of whether the ball 406 is in saltwater or freshwater (groundwater). As such, the valve 310 having a ball with a density less than 1 may be arranged at the top of the flexible tube 312 that is close to the dune and to the surface of the beach, e.g., as the last line of defense.

The valve 310 may restrict the flow of air or water in one direction during, for example, rising tide, king tide, or storm conditions, while allowing free or unrestricted flow of air and/or water in the opposite direction by enabling the ball 406 to rise and fall for opening and closing the first stop 404. The ball 406 may rise to the first stop 404 when upwardly-directed air pressure within the module 140 is above a threshold value, or based on the pressure of the water rising within the module 140. That is, the air or water applying an upward force (in the direction moving from opening 410 toward opening 409) in module 140 may move the ball 406 upward to block opening 404b and prevent further fluid flow through the valve 310. In particular, a storm or large waves moving rapidly inland may cause an increase in the air pressure or the water level in the module 140, elevating the ball 406 within the conduit 402. As such, the beach may behave like a normal beach during king tide, rising tide, or storms, restricting the excess inflow of water inland as if the modules 140 had not been installed in the beach. However, during falling tides, the valve 310 may open (without air or water pressure acting in the upward direction), allowing the ball 406 to fall by gravity toward the top of the second stop 408. In this configuration, water and/or air may flow through the conduit 402 and the module 140. As such, the air or water may travel freely down into the module 140 to promote one-direction pressure equalization and effective drainage of the beach during falling tides. The valve 310 may also be provided in the first flexible tube 312 or the second flexible tube 316 extending from the module 140. By providing the valve in the solid upper portion of the module 140, when placed vertically (relative to the surface), gravity may assist with the operation of valve 310 (particularly, by pulling ball 406 down during falling tide). By providing the valve 310 in the first flexible tube 312, in at least some embodiments, the valve 310 may be placed closer to the beach surface with minimum exposure to water, which may allow for a wide variation of valve types.

The valve 310 may include materials that are tolerant and/or resistant to saltwater, sand, and other particles or debris commonly found on a beach. The materials may include, but are not restricted to, high-density polyethylene (HDPE) or other forms of plastic, silicone, or rubber. The design of the valve 310 may require minimum service and may be self-cleaning through frequent movement of a moveable part (e.g., ball 406 or other movable obstruction) within the valve. If the valve 310 is a ball-type valve, the size of the ball 406, the weight of the ball 406, and the diameter of the conduit 402 in which the ball moves up or down may determine the amount of flow of air or water needed to move the ball 406 up to the first stop 404 and close the valve 310. The variability of the valve 310 design, materials, weight, and placement of valve 310, may allow a user to build the modules 140 and design installations tailored according to specific beach conditions. For example, on a high energy coast (e.g., a coast with large waves) the ball 406 may be heavier. Further, on special beaches such as a beach with a high tide difference, (e.g., several meters), a ball 406 that is moved only by pressure with a density slightly over 1 may be provided in the modules 140 installed in the mid beach. In the back beach, the modules 140 may have two or more valves 310. That is, the valve 310 arranged on the lower position may be provided in the same location as the valve 310 for the modules 140 installed in mid beach. However, the valve 310 arranged on the upper position may be provided higher in the flexible tube 312 with the density of the ball 406 being below 1. As such, the valve 310 on the upper position may close if the water level reaches the valve 310 inside the flexible tube 312. Furthermore, on a beach with high value hinterland where preventing flooding is always necessary, all of the modules on the dry beach (e.g., typically from mid beach and towards the dune) may include the ball 406 with a density below 1. The flexible tube 312 may also vary in lengths (e.g., from about 30 cm to over 1 m) based on the tidal range.

In one embodiment, the valve 310 may be electrically operated using a battery. For example, the valve 310 may incorporate an electrically controllable element (e.g., a flap) to open or close the hole 404b of the first stop 404 based on an electrical signal transmitted from a controller. The controller may be configured to control the electrically controllable element based on a predetermined condition (e.g., a timing or a weather condition detected by a sensor). The controller may also be configured to receive signals wirelessly. For example, the controller may automatically control the electrically controllable element to open or close the hole 404b of the first stop 404 based on weather forecast information that may be received wirelessly.

In an alternative embodiment shown in FIGS. 4C and 4D, the second stop 408 may include circumferentially spaced apart pins 408a-c extending radially inward from the inner surface of conduit 402. The pins 408a-c may be, for example, a third of the length of d1, or another suitable length. The pins 408a-c may also be configured to point downward in the conduit 402 toward the lower opening 410, as shown in FIG. 4B, effectively creating a constriction within conduit 402 that maintains ball 406 within valve 310. The arrangement of pins 408a-c may allow the ball 406 to rest in the center portion of the conduit 402, when the ball 406 falls on the pins 408a-c and ensure that the ball 406 gets sufficiently lifted to block the first stop 404. The arrangement shown in FIGS. 4C-4D may be used anywhere where this disclosure mentions valve 310.

Figure 5B:
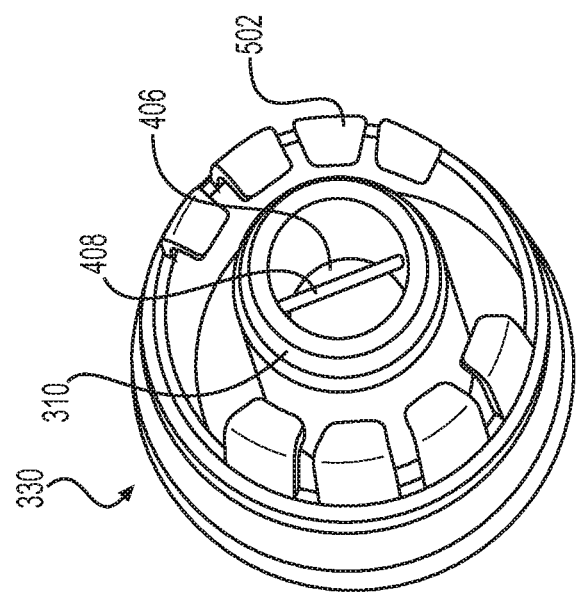
FIG. 5B depicts a second (bottom) side of an activatable valve, according to one or more embodiments.
Figure 5A:
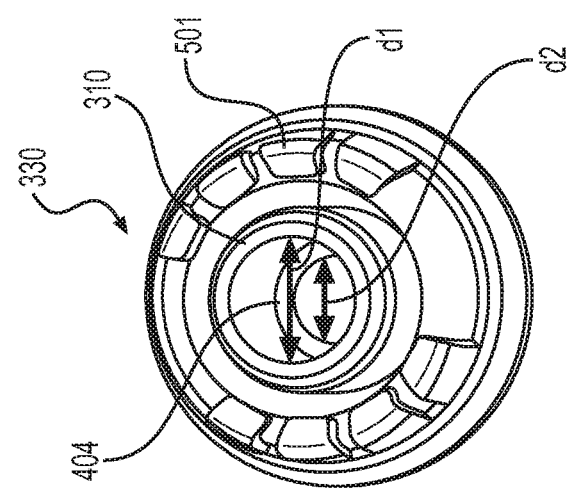
FIG. 5A depicts a first (top) side of an activatable valve, according to one or more embodiments.

FIGS. 5A and 5B depict different views of the housing 330 with the valve 310 arranged within the housing 330. FIG. 5A shows a first (top) side of the housing 330, and FIG. 5B shows a second (bottom) side opposite the first side of the housing 330. As shown in FIG. 5A, the housing 330 may include flanges 501 for securing the first flexible tube 312 to the conduit 402 of the valve 310. The flanges 501 may be elastic fingers arranged radially about the circumference of the housing 330 and may be flexible. The flanges 501 may apply a radially-inward directed force when the tube 312 is coupled to the valve 310, and that force may help maintain the valve 310 and the tube 312 together. Additionally, as shown in FIG. 5B, the housing 330 further includes the flanges 502 for securing the second flexible tube 316 to the conduit 402 of the valve 310. The flanges 502 may be substantially similar to the flanges 501.

Figure 6:
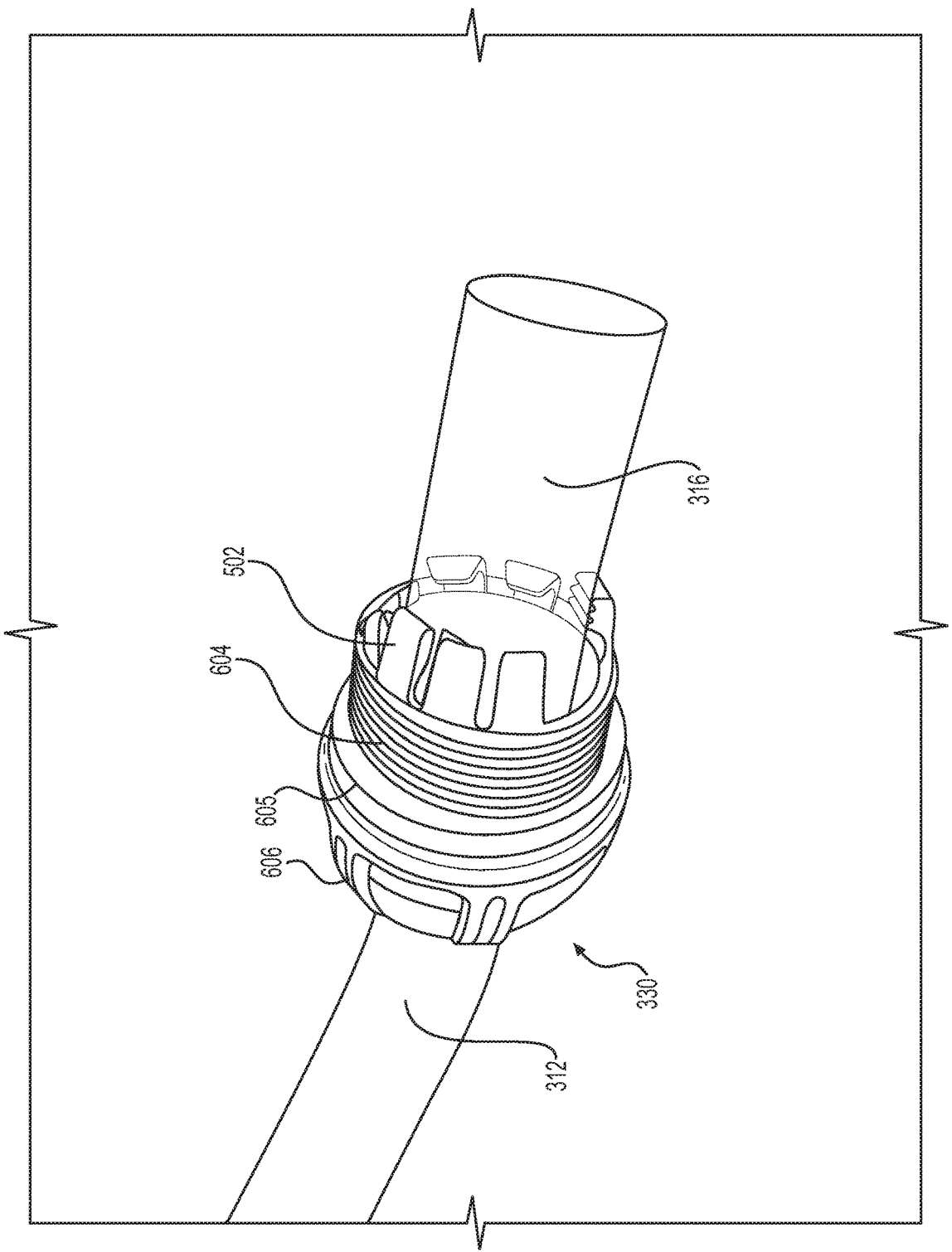
FIG. 6 depicts a housing of an activatable valve, according to one or more embodiments.

FIG. 6 depicts the housing 330 coupled to the first flexible valve 312 and the second flexible tube 316. The first flexible tube 312 may be coupled to the conduit 402 of the valve 310 at the first side of the housing 330. The second flexible tube 316 may be coupled to the conduit 402 of the valve 310 at the second side of the housing 330. The flanges 501, 502 may secure the first and second flexible tubes 312, 316 by applying inward pressure on the surfaces of the first and second flexible tubes 312, 316 when the first and second flexible tubes 312, 316 are coupled to the conduit 402 valve 310. The housing 330 may also include a ring 605 that may facilitate coupling of the housing 330 to the cap 308 shown in FIG. 3.

Figure 7:
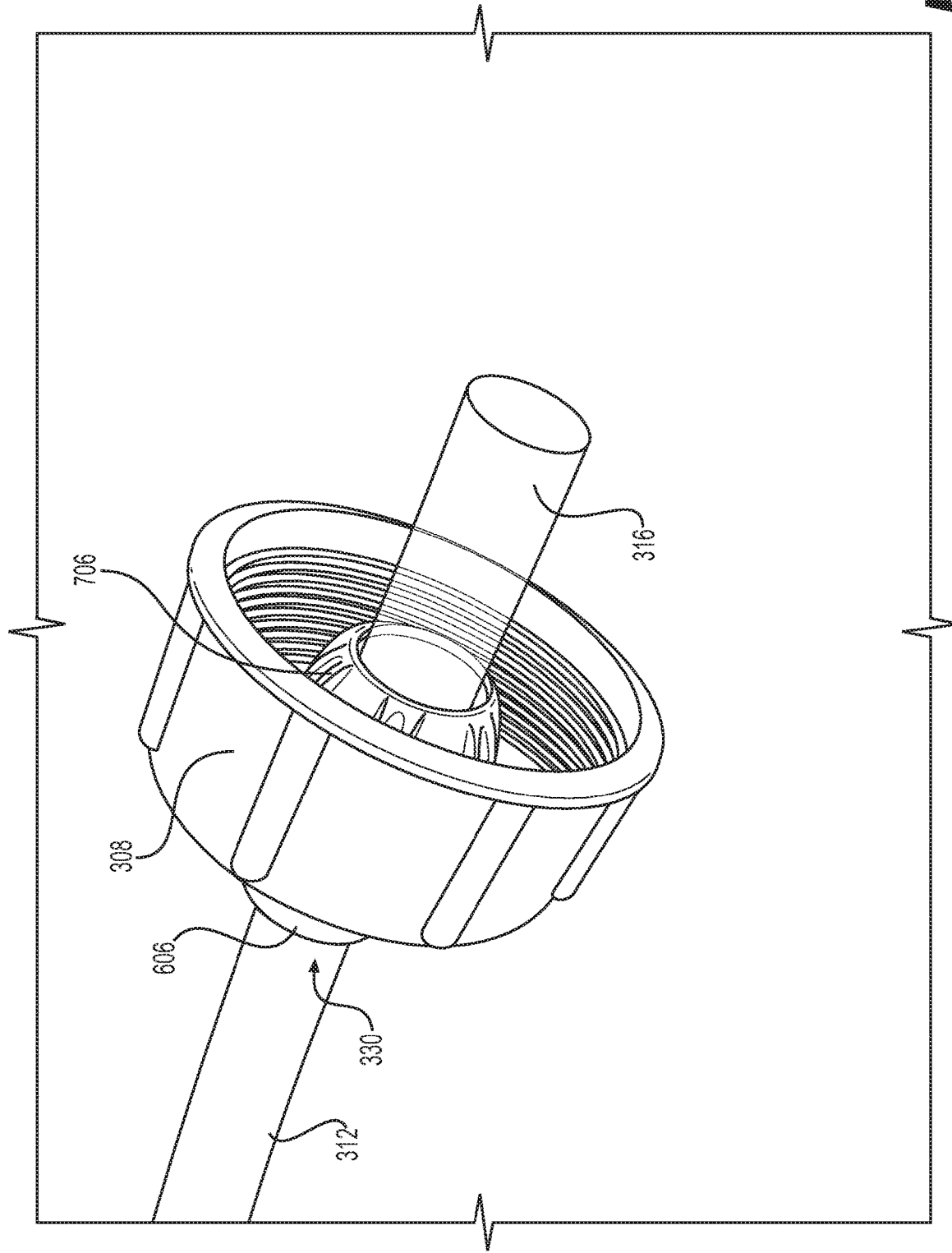
FIG. 7 depicts a housing of activatable valve and cap, according to one or more embodiments.

FIG. 7 shows the housing 330 coupled to the cap 308. Upon coupling the first and second flexible tubes 312, 316 to the valve 310 or the housing 330, the valve 310 may be coupled to the cap 308 by inserting the second flexible tube 316 through an upper opening of the cap 308. A securing mechanism 706 may then be placed around the second flexible tube 316, and may be coupled to a portion of valve 310. In the embodiment shown, mechanism 706 may be a cap having internal threads that are screwed onto threads 604 on the outer surface of the valve 310 to secure the cap 308 to the valve 310. Of course, other coupling mechanism also are contemplated. The securing mechanism 706 may have a larger outer diameter or dimension than the opening of the cap 308, to prevent the securing mechanism 706 from going through the opening of the cap 308. The securing mechanism 706 also may be configured to provide a radially-inward directed force to help secure the second flexible tube 316. Furthermore, a securing mechanism 606 (referring to FIG. 6) may be provided on the first side of the valve 310 to provide a radially-inward directed force when tightened to secure the first flexible tube 312 on the first side of the valve 310.

Generally, drainage modules on a beach may be buried below the surface of the top sand layer at installation. However, such drainage modules may become exposed after severe tidal and coastal weather conditions. An exposed drainage module may cause a beach visitor to trip over the rigid tube of the drainage module. In addition, a beach cleaning machine may hit the top of the drainage module that is exposed or nearly exposed while tilling or cleaning the top few inches of the beach. When the exposed or nearly exposed module is hit by the beach cleaning machine, the module may get capped resulting in sharp edges and risk of body harm. Further, it will allow sand to enter and fill the module, A module that is filled with sand may render the module ineffective, causing delays in producing desired results on the beach, or preventing achieving the desired results altogether.

In an exemplary embodiment of the present disclosure, the first flexible tube 312 of the module 140 may be rigid enough to stand on its own for at least about 4 hours in at least about 50 degrees Celsius when approximately about 10 to about 20 cm (about 4 to about 8 inches) of the first flexible tube 312 is exposed above the surface of the top sand layer 105. The diameter of the first flexible tube 312 may be about 3 to about 50 mm (about 0.125 inches to about 2 inches), preferably about 13 mm to about 25 mm (about 0.5 inches to about 1 inch). Of course, these dimensions are only exemplary, and it is contemplated that first flexible tube 312 may operate in other dimensions as well. The first flexible tube 312 may include materials that tolerate a coastal environment including saltwater, sun, heat, and frost. The first flexible tube 312 may include a chemically resistant material and a material that is non-stick to lime/scaling, sand, mud, and other organic materials. Further, the first flexible tube 312 may be made from materials including, but not restricted to, plastic, rubber silicone or a combination of materials. The first flexible tube 312 may be green, blue, orange or any other suitable color, or even transparent. As such, an exposed module 140 with the first flexible tube 312 may not be hazardous to beach visitors as the first flexible tube 312 may bend and flex when the beach visitors come in contact with the exposed 140. Further, if the first flexible tube 312 comes into contact with a beach cleaning machine, the first flexible tube 312 may bend or flex to prevent damage to the first flexible tube 312 while not effecting any functionality of the module 140. Therefore, the first flexible tube 312 may prevent damage to the installed modules 140 and the beach cleaning machines, and also may reduce tilling or cleaning time compared to the conventional drainage modules.

Figure 8:
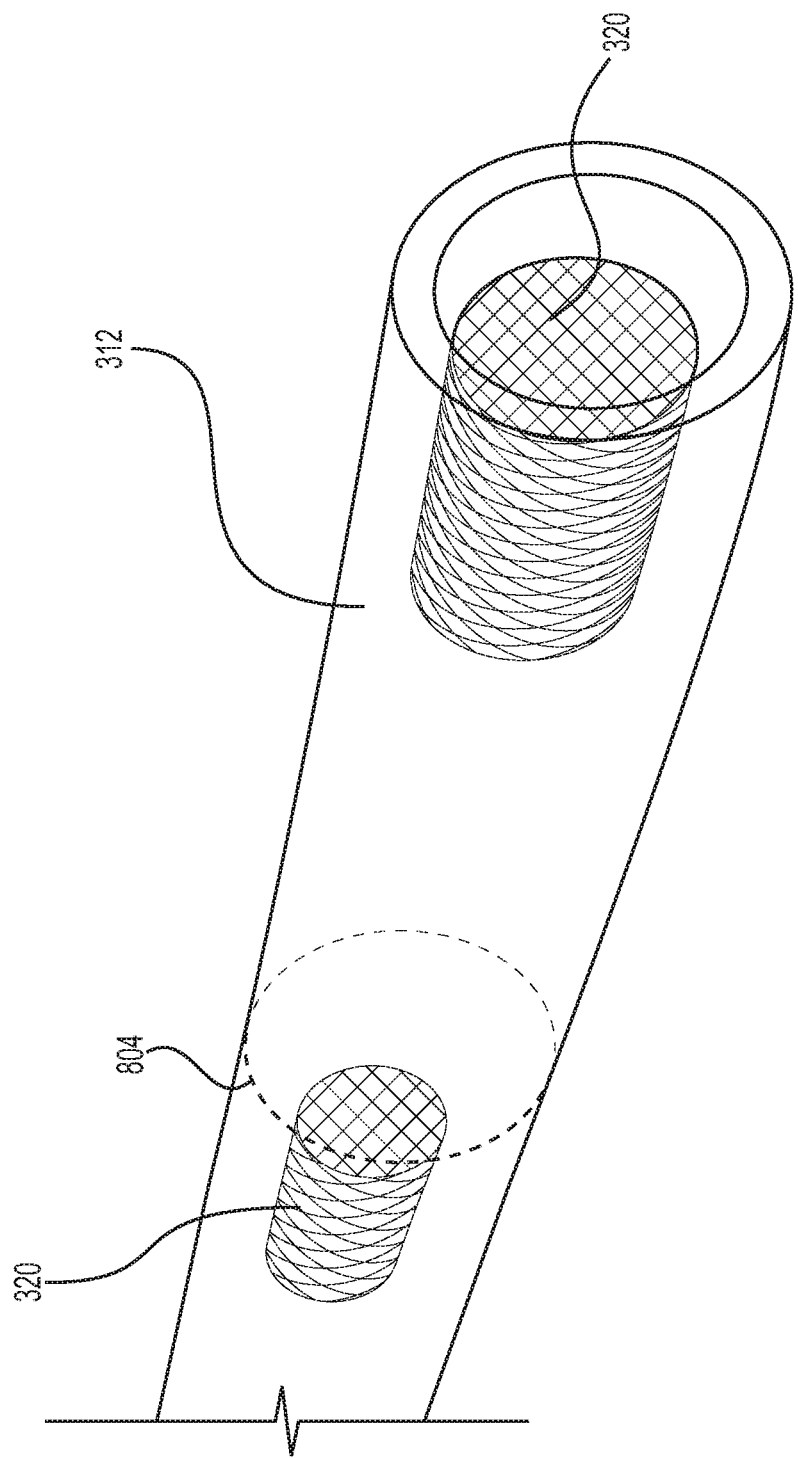
FIG. 8 depicts a flexible tube of a drain control module, according to one or more embodiments.

Exposed rubber or plastic tubes of module 140 protruding from the beach may be tempting for a beach visitor to try to remove by pulling on it. As such, to prevent the first flexible tube 312 and the valve 310 from being removed or damaged by the beach visitors, according to an exemplary embodiment as shown in FIG. 8, the first flexible tube 312 may have precut slits 804 (or perforations) on the surface of the first flexible tube 312 (at an intermediate location along its longitudinal axis). That is, the first flexible tube 312 may break off above the valve 310 to maintain the function of the module 140. Further, the first flexible tube 312 may have an identification number of the module 140 and a writing on the surface to explain the function of the module 140. Furthermore, in an exemplary embodiment, the first flexible tube 312 may include one or more filters 320. For example, one filter 320 may be provided adjacent the uppermost opening of the first flexible tube (i.e., in the part of flexible tube 312 configured to break away if pulled with a sufficient force), and another filter 320 may be disposed underneath and adjacent the precut slits or perforation 804 as shown in FIG. 8. Thus, even if the uppermost section of the flexible tube 312 is pulled away, the lower remaining section would still include at least one filter 320. It is further contemplated that flexible tube 312 may include a plurality of longitudinally spaced apart slits or perforations 804, so that flexible tube 312 may withstand numerous instances of tampering by beach visitors. For example, flexible tube 312 could include 2, 3, or more separate slits of perforations 804 and at least as many filters 320. Each filter may be disposed below and adjacent to one of the slits or perforations 804.

Figure 9A:
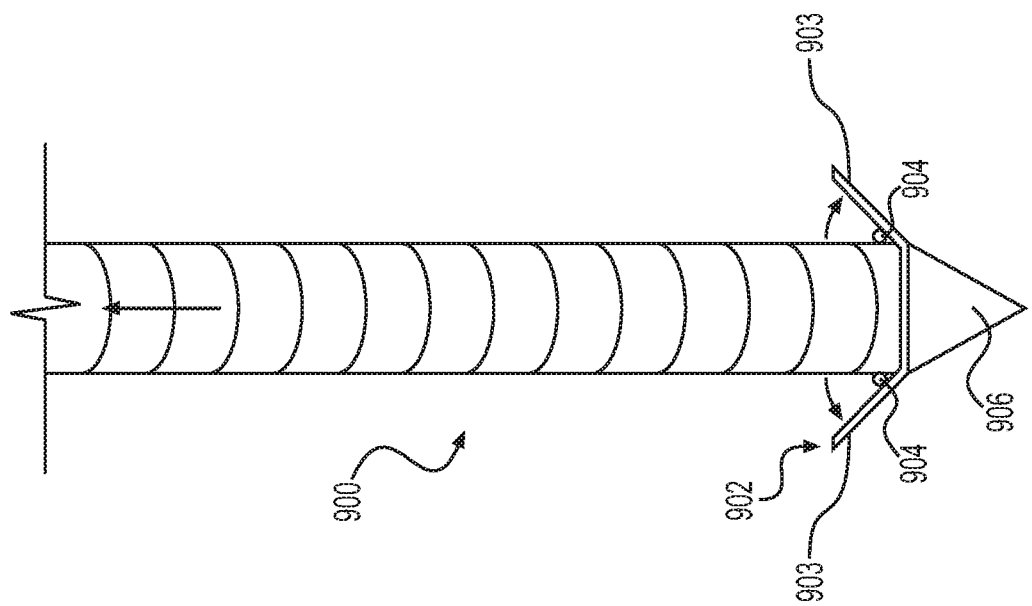
FIGS. 9A and 9B depict a drainage control module having an anchoring element, according to one or more embodiments.

An exposed module 140 on a beach may be tempting for a beach visitor to try to remove the entire module out of the beach by pulling on it. That is, a strong person may be able to pull the exposed module 140 up out of the beach as there may be limited resistance due to the straight tubular shape of the module 140. FIG. 9A depicts a module 900 with an anchoring device 902 coupled to, at, or adjacent, a distal end of the module 900. The module 900 may comprise a hollow tube substantially similar to the tube 302. Further, the module 900 may incorporate some or all of the features of the module 140 or the seaward module 150 according to embodiments of the present disclosure. As shown in FIG. 9A, the module 900 may include a pointed tip 906 on the distal end of the module 900 to facilitate the insertion of the module 900 into the top sand layer 105 and the different layers underneath the top sand layer 105. The pointed top may point away from the distal end of module 900. Further, the anchoring device 902 may comprise flaps 903 and stops 904 disposed between the flaps 903 and the body of module 900. In some example, the stops 904 may include foam elements or the like. The stops 904 may prevent the flaps of the anchoring device 902 from folding flat against the tube of the module 900. During installation, as the module 900 is being inserted down into the different layers underneath the top sand layer 105, the flaps 903 on the anchoring device 902 may fold close to the surface of the module 900. However, if the module 900 is pulled upward, after installation (FIG. 9B), the flaps 903 on the anchoring device 902 may open and add a substantial amount of resistance to prevent the module 900 from being pulled out in the upward direction. As such, a beach visitor may be inhibited or prevented from removing the module 900 from underneath the top sand layer 105 by hand.

Generally, when rows of drainage modules are installed, the excess water in the hinterland may start to move through the beach and exit at the drainage module closest to sea that may be placed at the low water level. Change in beach floor elevation may result in the top of the drainage module being placed at the low water line, for example, from less than 10 cm to over 60 cm below the sand, and water may exit through the opening at the top of the drainage module. The flow of water from the drainage module closest to the sea upwards into the sand underneath the sea floor may cause flotation of the sand above the drainage module especially when the opening is close to the sand surface, potentially causing a condition like quicksand. This suspended sand may be easily removed by current and waves, causing erosion. The erosion caused by this effect may be highest at project start (after initial installment of the modules in a beach) when the high pressure from the hinterland is first released, but may continue for weeks or months until the excess groundwater pressure is equalized.

In an exemplary embodiment according to the present disclosure, a flexible tube of a seaward module 150 may be placed beyond the lower low water line and will, under all conditions, be under water. That is, at low tide, the flexible tube of the seaward module 150 may be under the surface of the water, and at mean or high tide, the flexible tube of the seaward module 150 may be up to about several feet below the surface of the water. The seaward module 150 having the flexible tube may protrude from the bottom of the seafloor and into the open water. Indeed, the excess drained water from the beach and/or hinterland may bypass the sand on the sea floor and go directly into the sea from the flexible tube of the seaward module 150 and prevent the phenomenon of flotation of the sand. Therefore, the sand may stay firm and have a better resistance to erosion.

In an exemplary embodiment according to present disclosure, the seaward module 150 may incorporate the flexible tubes 312, 316 similarly to the module 140. To prevent a beach visitor from attempting removing the flexible tube 312 or the seaward module 150, the flexible tube 312 may be camouflaged. The flexible tube may be transparent, or may be shaped like sea weed. Since the seaward module 150 may only need to be effective for a few months the flexible tube 312 may be made from water soluble material. For example, the water soluble material may be configured to degrade after a predetermined amount of time, such as, e.g., one month, or any other suitable amount of time.

Figure 9B:
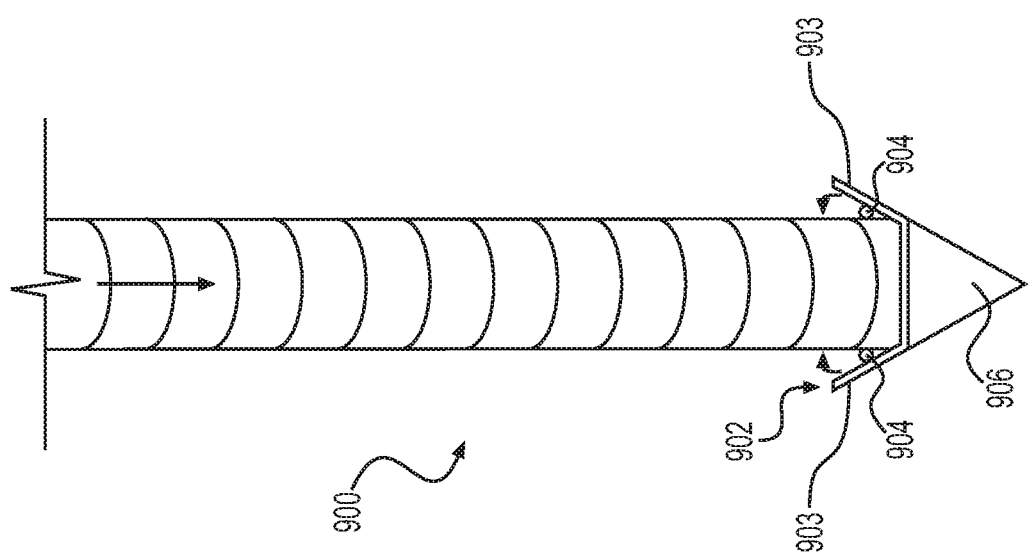

Another problem in the oceans and on beaches is the rising amount of plastic waste. This has led the usage ban on plastic bags, cups, straws, etc. in many areas. It is possible that, over time, the use of plastic materials may be restricted or banned on beaches. As such, there is a drive for using natural materials where possible. In accordance with an exemplary embodiment of the present disclosure, the module 140 may be made from a natural material (e.g., wood). Several types of wood may be used for the module 140. As the tube 302 of the module 140 needs to be hollow, a hole may be drilled in wood, or thin layers of wood may be used to shape a hollow tube. In an exemplary embodiment, bamboo may be used for the tube 302 of the module 140. Bamboo has natural strength similar to plastic modules and is rounded and hollow. Further, bamboo may only require the internal separations to be removed. The pointed tip 906 as shown in FIGS. 9A and 9B may also be made of wood at the bottom of a wooden tube of the module 140, and the closed top/cap for the module 140 may also be made from wood, cork or other organic materials. Slits may be added to the surface of the wooden tube of the module 140, but the slits may allow unwanted access of microorganisms that may decompose the wooden tube. In an exemplary embodiment, the wooden tube (wood or bamboo) of the module 140 may be impregnated with chemicals (e.g., using $CO_2$ to achieve extraordinary impregnation using a minimum amount of chemicals) to avoid degradation. The chemicals used for impregnating the module 140 may include propiconazole, tebuconazole, and iodopropynyl butylcarbamate (IPBC).

The use of chemicals may be minimized for environmental reasons while protecting the wooden tube of the module 140. In an exemplary embodiment, an environmentally-friendly supercritical carbon dioxide technology as developed by FLS Miljo called Superwood may be employed. The wooden tube of the module 140 may be placed in a high pressure chamber and chemicals including $CO_2$, and heat may be added. When the supercritical state is reached, the active ingredients may be dissolved in $CO_2$ and penetrate and preserve the wood to the core with minimal use of chemicals. In another exemplary embodiment, a methodology presented by Dr. Liangbing Hu from the University of Maryland may be used where the wood is made much denser and stronger while being less affected by degradation.

In view of the above, it will be seen that the several objects of the disclosure are achieved and other advantageous results attained. As various changes could be made in the above constructions, products, and methods without departing from the scope of the disclosure, it is intended that all matter contained in the above description and shown in the accompanying drawings shall be interpreted as illustrative and not in a limiting sense.

What is claimed is:

1. A drainage device, comprising:
a conduit extending from a bottom end toward a top end; and
a valve coupled to the conduit, the valve including:
a first stop, the first stop having an opening; and
an obstruction within the conduit, wherein:
in a first configuration, the obstruction is spaced apart from the opening, enabling fluid to flow through the first stop and through the conduit; and
in a second configuration, the obstruction is configured to block the opening to prevent fluid flow through the first stop and through the conduit, wherein the obstruction is configured to move from the first configuration to the second configuration in response to (1) fluid pressure acting in a direction from the bottom end toward the top end of the conduit, or (2) when a fluid having a higher density than the obstruction is disposed within the valve;
a flexible tube in fluid communication with the conduit, and extending away from the top end of the conduit; and
a filter coupled to the flexible tube, wherein the filter is fluid-permeable and is configured to prevent debris from entering the flexible tube.

2. The drainage device of claim 1, wherein the obstruction is a ball having a diameter larger than a diameter of the opening of the first stop.

3. The drainage device of claim 1, wherein the valve further includes:
a second stop, wherein the obstruction is positioned between the first stop and the second stop, and the second stop is configured to maintain the obstruction in the valve, and also is configured to allow fluid to flow through the second stop, wherein the second stop is a rod, a beam, a pin, several pins, or a screen.

4. The drainage device of claim 1, wherein the obstruction is configured to transition from the second configuration to the first configuration when the fluid pressure acting in the direction from the bottom end toward the top end of the conduit is less than a force of gravity acting on the obstruction.

5. The drainage device of claim 1, wherein the drainage device does not include any electronic component.

6. The drainage device claim 1, wherein the drainage device is configured to operate the obstruction to open and close the opening of the first stop based on an electrical signal; and/or
wherein the obstruction is configured to automatically open or close the first stop based on a predetermined weather condition.

7. The drainage device of claim 1, wherein the conduit includes a plurality of openings extending through an outer surface and an inner surface of the conduit, wherein fluid is configured to flow through the plurality of openings.

8. The drainage device of claim 1, wherein the drainage device is made from natural materials, the natural materials being wood or bamboo.

9. The drainage device of claim 1, wherein the drainage device comprises materials that are impregnated using $CO_2$.

10. The drainage device of claim 1, wherein the flexible tube comprises a perforation between a first part and a second part of the flexible tube, wherein the first part of the tube is directly coupled to the conduit, wherein, in response to a pulling force applied to the second part of the flexible tube, the second part is configured to separate from the first part at the perforation.

11. The drainage device of claim 10, further including a first filter coupled to the first part of the flexible tube, and a second filter coupled to the second part of the flexible tube, wherein each of the first filter and the second filter is fluid-permeable and is configured to prevent debris from entering the first part and the second part, respectively.

12. A drainage device, comprising:
a conduit extending from a bottom end toward a top end;
a valve coupled to the conduit, the valve including:
  a first stop, the first stop having an opening; and
  an obstruction within the conduit, wherein:
    in a first configuration, the obstruction is spaced apart from the opening, enabling fluid to flow through the first stop and through the conduit; and
    in a second configuration, the obstruction is configured to block the opening to prevent fluid flow through the first stop and through the conduit, wherein the obstruction is configured to move from the first configuration to the second configuration in response to (1) fluid pressure acting in a direction from the bottom end toward the top end of the conduit, or (2) when a fluid having a higher density than the obstruction is disposed within the valve; and
a pointed tip extending away from the bottom end of the conduit.

13. A drainage device, comprising:
a conduit extending from a bottom end toward a top end;
a valve coupled to the conduit, the valve including:
  a first stop, the first stop having an opening; and
  an obstruction within the conduit, wherein:
    in a first configuration, the obstruction is spaced apart from the opening, enabling fluid to flow through the first stop and through the conduit; and
    in a second configuration, the obstruction is configured to block the opening to prevent fluid flow through the first stop and through the conduit, wherein the obstruction is configured to move from the first configuration to the second configuration in response to (1) fluid pressure acting in a direction from the bottom end toward the top end of the conduit, or (2) when a fluid having a higher density than the obstruction is disposed within the valve;
two or more flaps at or adjacent the bottom end of the conduit, wherein:
  each flap includes a first end and a second end, wherein the second end of each flap is positioned closer to the top end of the conduit than the first end of each flap; and
  the second end of each flap is positioned further away from an outer surface of the conduit than the first end of each flap;
one or more blocking members, wherein:
  each of the one or more blocking members is disposed between the outer surface of the conduit and one of the two or more flaps; and
  each of the one or more blocking members is configured to prevent the one of the two or more flaps from extending substantially parallel to the outer surface of the conduit.

14. A drainage device, comprising:
a conduit extending from a bottom end toward a top end; and
a valve coupled to the conduit, the valve being configured to:
  in a first configuration, enable fluid to flow through the valve and through the conduit from the top end toward the bottom end; and
  in a second configuration, prevent fluid flow through the valve and through the conduit; and
a flexible tube in fluid communication with the conduit, and extending away from the top end of the conduit, wherein:
  the flexible tube comprises a perforation between a first part and a second part of the flexible tube;
  the first part of the tube is directly coupled to the conduit; and
  in response to a pulling force applied to the second part of the flexible tube, the second part is configured to separate from the first part at the perforation.

15. The drainage device of claim 14, further including a first filter coupled to the first part of the flexible tube, and a second filter coupled to the second part of the flexible tube, wherein each of the first filter and the second filter is fluid-permeable and is configured to prevent debris from entering the first part and the second part, respectively, wherein the conduit includes a plurality of openings extending through an outer surface and an inner surface of the conduit, wherein the conduit is hollow, and wherein fluid is configured to flow through the plurality of openings.

* * * * *